(12) United States Patent
Kaufman

(10) Patent No.: US 8,299,079 B2
(45) Date of Patent: Oct. 30, 2012

(54) PREPARATIONS AND METHODS FOR AMELIORATING OR REDUCING PRESBYOPIA

(76) Inventor: Herbert E. Kaufman, Sarasota, FL (US)

( * ) Notice: Subject to any disclaimer, the term of this patent is extended or adjusted under 35 U.S.C. 154(b) by 0 days.

(21) Appl. No.: 12/973,479

(22) Filed: Dec. 20, 2010

(65) Prior Publication Data

US 2011/0152274 A1    Jun. 23, 2011

Related U.S. Application Data

(63) Continuation-in-part of application No. 12/785,734, filed on May 24, 2010.

(60) Provisional application No. 61/180,521, filed on May 22, 2009, provisional application No. 61/291,206, filed on Dec. 30, 2009.

(51) Int. Cl.
- *A01N 43/58* (2006.01)
- *A01N 43/60* (2006.01)
- *A01N 43/52* (2006.01)
- *A01N 43/50* (2006.01)

(52) U.S. Cl. ............ 514/249; 514/397; 514/235.8; 514/393

(58) Field of Classification Search .............. 514/249, 514/397, 393, 235.8
See application file for complete search history.

(56) References Cited

U.S. PATENT DOCUMENTS

| | | |
|---|---|---|
| 4,001,388 A | 1/1977 | Shell |
| 4,008,719 A | 2/1977 | Theeuwes et al. |
| 4,014,334 A | 3/1977 | Theeuwes et al. |
| 4,014,335 A | 3/1977 | Arnold |
| 4,115,544 A | 9/1978 | Shell |
| 4,136,173 A | 1/1979 | Pramoda et al. |
| 4,136,177 A | 1/1979 | Lin et al. |
| 4,136,178 A | 1/1979 | Lin et al. |
| 4,186,184 A | 1/1980 | Zaffaroni |
| 4,271,143 A | 6/1981 | Schoenwald et al. |
| 4,407,792 A | 10/1983 | Schoenwald et al. |
| 4,459,309 A | 7/1984 | Chiou |
| 4,474,751 A | 10/1984 | Haslam et al. |
| 4,652,571 A | 3/1987 | Croom, Jr. et al. |
| 4,661,509 A | 4/1987 | Gordon et al. |
| 4,668,506 A | 5/1987 | Bawa |
| 4,713,244 A | 12/1987 | Bawa et al. |
| 4,931,279 A | 6/1990 | Bawa et al. |
| 4,952,212 A | 8/1990 | Booth et al. |
| 5,010,056 A | 4/1991 | Boghen et al. |
| 5,084,281 A | 1/1992 | Dillon |
| 5,153,205 A | 10/1992 | Lotti |
| 5,182,102 A | 1/1993 | DeSantis, Jr. et al. |
| 5,229,127 A | 7/1993 | McKinzie |
| 5,352,698 A | 10/1994 | Santini |
| 5,360,801 A | 11/1994 | Laties et al. |
| 5,384,243 A | 1/1995 | Gutkind et al. |
| 5,422,116 A | 6/1995 | Yen et al. |
| 5,459,133 A | 10/1995 | Neufeld |
| 5,459,140 A | 10/1995 | Grammer |
| 5,474,783 A | 12/1995 | Miranda et al. |
| 5,538,983 A | 7/1996 | Buxbaum et al. |
| 5,569,464 A | 10/1996 | Endo et al. |
| 5,599,836 A | 2/1997 | Santini |
| 5,624,962 A | 4/1997 | Takeuchi et al. |
| 5,656,286 A | 8/1997 | Miranda et al. |
| 5,677,327 A | 10/1997 | Gil et al. |
| 5,679,713 A | 10/1997 | Hahnenberger |
| 5,686,100 A | 11/1997 | Wille et al. |
| 5,688,510 A | 11/1997 | Nakamichi et al. |
| 5,704,369 A | 1/1998 | Scinto et al. |
| 5,773,466 A | 6/1998 | Santini |
| 5,776,916 A | 7/1998 | Gramer |
| 5,811,446 A | 9/1998 | Thomas |
| 5,817,630 A | 10/1998 | Hofmann et al. |
| 5,843,016 A | 12/1998 | Lugnani et al. |
| 5,843,979 A | 12/1998 | Wille et al. |
| 5,858,410 A | 1/1999 | Muller et al. |
| 5,858,996 A | 1/1999 | Tsao |
| 5,861,431 A | 1/1999 | Hildebrand et al. |
| 5,908,866 A | 6/1999 | Hahnenberger |
| 5,912,010 A | 6/1999 | Wille et al. |
| 5,948,401 A | 9/1999 | Donabedian et al. |
| 5,977,174 A | 11/1999 | Bradley et al. |
| 6,011,062 A | 1/2000 | Schneider et al. |

(Continued)

FOREIGN PATENT DOCUMENTS

WO    WO 2004108135    12/2004

(Continued)

OTHER PUBLICATIONS

Minims (Minims Pilocarpine Eye Drops, product information, 1999, p. 1-4).*
Kesler et al. (J Cataract Refract Surg, 20, 2004, 1707-1710).*
Tornqvist, "Effect of Topical Carbachol on the Pupil and Refraction in Young and Presbyopic Monkeys," Investigative Ophthalmology, vol. 5, No. 2, (1966), pp. 186-195.
Shiuey et al., "Cardiovascular Effects of Commonly Used Ophthalmic Medications," Clin. Cardiol., vol. 19, (1996), pp. 5-8.
Alpha 1 Blocker (http://en.wikipedia.org/wiki/Alpha-1_blocker, (2011), pp. 1-3.

(Continued)

*Primary Examiner* — Sreeni Padmanabhan
*Assistant Examiner* — Uma Ramachandran
(74) *Attorney, Agent, or Firm* — Brinks Hofer Gilson & Lione

(57) ABSTRACT

This application relates to the use of one or more parasympathomimetic drugs in combination with one or more alpha agonists to create optically beneficial miosis to, for example, temporarily treat presbyopia. The invention provides a pharmaceutical preparation comprising a therapeutically effective amount of one or more parasympathomimetic drugs or cholinesterase inhibitors, or a pharmaceutically acceptable salt thereof, in combination with one or more alpha agonists or antagonists, or a pharmaceutically acceptable salt thereof. The invention further provides for a method for treating, ameliorating or reducing presbyopia of a patient having an eye, comprising administering to said eye a pharmaceutically effective amount of the ophthalmic preparation.

6 Claims, 2 Drawing Sheets

U.S. PATENT DOCUMENTS

| | | | |
|---|---|---|---|
| 6,024,976 A | 2/2000 | Miranda et al. |
| 6,043,273 A | 3/2000 | Duhaylongsod |
| 6,060,454 A | 5/2000 | Duhaylongsod |
| 6,066,675 A | 5/2000 | Wen et al. |
| 6,087,394 A | 7/2000 | Duhaylongsod |
| 6,127,410 A | 10/2000 | Duhaylongsod |
| 6,164,282 A | 12/2000 | Gwon et al. |
| 6,174,524 B1 | 1/2001 | Bawa et al. |
| 6,184,250 B1 | 2/2001 | Klimko et al. |
| 6,194,415 B1 | 2/2001 | Wheeler et al. |
| 6,242,442 B1 | 6/2001 | Dean et al. |
| 6,248,741 B1 | 6/2001 | Wheeler et al. |
| 6,273,092 B1 | 8/2001 | Nolan |
| 6,291,466 B1 | 9/2001 | Gwon et al. |
| 6,294,553 B1 | 9/2001 | Gil et al. |
| 6,294,563 B1 | 9/2001 | Garst |
| 6,313,155 B1 | 11/2001 | Sponsel |
| 6,316,441 B1 | 11/2001 | Dean et al. |
| 6,329,369 B1 | 12/2001 | Chow et al. |
| 6,410,045 B1 | 6/2002 | Schultz et al. |
| 6,410,544 B1 | 6/2002 | Gwon et al. |
| 6,414,018 B1 | 7/2002 | Duhaylongsod |
| 6,420,407 B1 | 7/2002 | Horn |
| 6,441,047 B2 | 8/2002 | DeSantis, Jr. |
| 6,458,376 B1 | 10/2002 | Meadows |
| 6,511,817 B1 | 1/2003 | Lynch et al. |
| 6,528,520 B2 | 3/2003 | Clemens |
| 6,544,927 B2 | 4/2003 | Burns |
| 6,551,584 B2 | 4/2003 | Bandyopadhyay et al. |
| 6,562,563 B1 | 5/2003 | Murphy et al. |
| 6,610,713 B2 | 8/2003 | Tracey |
| 6,649,625 B2 | 11/2003 | Azuma et al. |
| 6,664,286 B1 | 12/2003 | May et al. |
| 6,673,812 B1 | 1/2004 | Azuma et al. |
| 6,711,436 B1 | 3/2004 | Duhaylongsod |
| 6,800,668 B1 | 10/2004 | Odidi et al. |
| 6,806,285 B1 | 10/2004 | May et al. |
| 6,814,976 B1 | 11/2004 | Hille et al. |
| 6,846,831 B2 | 1/2005 | Clemens |
| 6,919,310 B2 | 7/2005 | Clemens |
| 6,949,518 B1 | 9/2005 | Chu et al. |
| 6,956,036 B1 | 10/2005 | May et al. |
| 7,001,615 B1 | 2/2006 | Singh et al. |
| 7,012,090 B1 | 3/2006 | May et al. |
| 7,030,149 B2 | 4/2006 | Chang et al. |
| 7,074,827 B2 | 7/2006 | Ueno |
| 7,265,117 B2 | 9/2007 | Espino et al. |
| 7,294,646 B2 | 11/2007 | Garcia et al. |
| 7,320,976 B2 | 1/2008 | Chang et al. |
| 7,323,463 B2 | 1/2008 | Chang et al. |
| 7,345,065 B2 | 3/2008 | Gil et al. |
| 7,371,534 B2 | 5/2008 | Kauffman et al. |
| 7,384,651 B2 | 6/2008 | Hille et al. |
| 7,439,241 B2 | 10/2008 | DeJovin et al. |
| 7,494,983 B2 | 2/2009 | Chen et al. |
| 7,528,163 B2 | 5/2009 | Doherty et al. |
| 7,534,795 B2 | 5/2009 | Ruckmick et al. |
| 7,560,100 B2 | 7/2009 | Pinchasi et al. |
| 7,563,816 B2 | 7/2009 | Doherty et al. |
| 7,572,776 B2 | 8/2009 | Yu et al. |
| 7,576,122 B2 | 8/2009 | Shen et al. |
| 7,589,057 B2 | 9/2009 | Chang et al. |
| 7,642,258 B2 | 1/2010 | Chang et al. |
| 7,645,588 B2 | 1/2010 | Roos et al. |
| 7,749,730 B2 | 7/2010 | Bryant et al. |
| 2001/0047012 A1 | 11/2001 | Desantis, Jr. |
| 2002/0197300 A1 | 12/2002 | Schultz et al. |
| 2003/0036535 A1* | 2/2003 | Nolan .................. 514/114 |
| 2003/0125351 A1 | 7/2003 | Azuma et al. |
| 2004/0116524 A1 | 6/2004 | Cohen et al. |
| 2004/0137068 A1 | 7/2004 | Bhushan |
| 2004/0176408 A1 | 9/2004 | Horn |
| 2004/0192647 A1 | 9/2004 | Babizhayev |
| 2004/0224010 A1 | 11/2004 | Hofland et al. |
| 2004/0247681 A1 | 12/2004 | Ellis et al. |
| 2005/0085508 A1 | 4/2005 | Fukutomi et al. |
| 2005/0130906 A1 | 6/2005 | Matier et al. |
| 2005/0131025 A1 | 6/2005 | Matier et al. |
| 2005/0239871 A1 | 10/2005 | Hellberg et al. |
| 2005/0250788 A1 | 11/2005 | Tu et al. |
| 2006/0106106 A1 | 5/2006 | Glennon et al. |
| 2006/0166879 A1 | 7/2006 | Bhushan et al. |
| 2006/0172972 A1 | 8/2006 | Bhushan et al. |
| 2006/0177430 A1 | 8/2006 | Bhushan et al. |
| 2006/0194874 A1 | 8/2006 | Menotti et al. |
| 2006/0233859 A1 | 10/2006 | Whitcup et al. |
| 2006/0233860 A1 | 10/2006 | Chang et al. |
| 2006/0257452 A1 | 11/2006 | Hughes et al. |
| 2006/0292189 A1 | 12/2006 | Xia et al. |
| 2007/0053964 A1 | 3/2007 | Isowaki et al. |
| 2007/0059274 A1 | 3/2007 | Asgharian et al. |
| 2007/0122450 A1 | 5/2007 | Osio Sancho |
| 2007/0129441 A1 | 6/2007 | Koulen |
| 2007/0275098 A1 | 11/2007 | Banks |
| 2008/0085263 A1 | 4/2008 | Thuresson et al. |
| 2008/0107738 A1 | 5/2008 | Philips et al. |
| 2008/0112922 A1 | 5/2008 | Hughes et al. |
| 2008/0131484 A1 | 6/2008 | Robinson et al. |
| 2008/0300277 A1 | 12/2008 | Fetz et al. |
| 2009/0156606 A1* | 6/2009 | Sharma .................. 514/249 |

FOREIGN PATENT DOCUMENTS

| | | |
|---|---|---|
| WO | WO 2005115375 | 12/2005 |
| WO | WO 2005117830 | 12/2005 |
| WO | WO 2007011874 | 1/2007 |
| WO | WO 2008042619 | 4/2008 |
| WO | WO 2008075149 | 6/2008 |
| WO | WO 2008083118 | 7/2008 |

OTHER PUBLICATIONS

Adrenergic Agonists (Chapter 17, http://www.coursewareobjects.com/objects/evolve/E2/book_pages/lehne/images/Ch17_AdrenergicAgonists.pdf, (2011), pp. 150-162.

Agarwal, Refractive Surgery Nightmares, vol. 301, (2007), pp. 1-4.

* cited by examiner

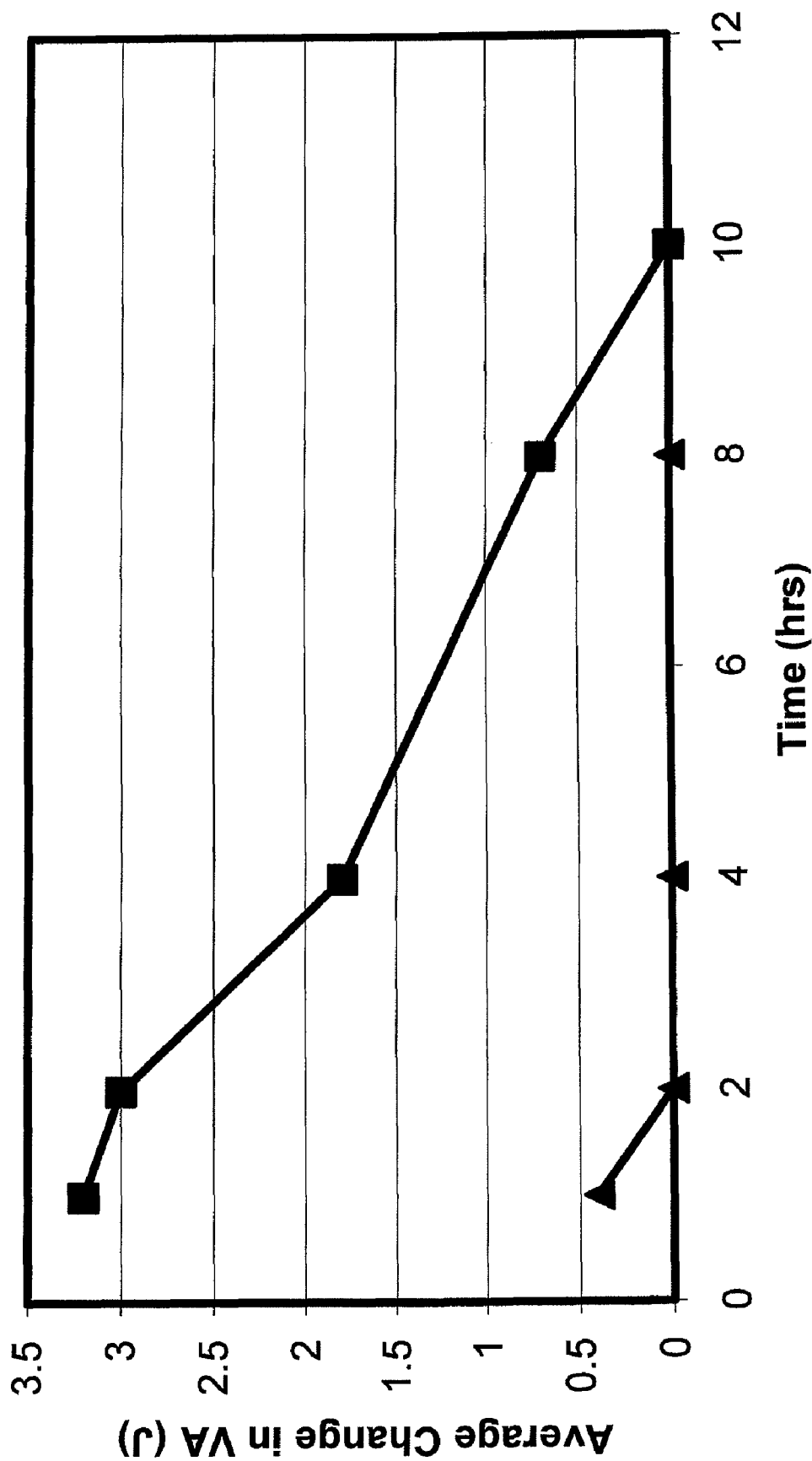

PREPARATIONS AND METHODS FOR AMELIORATING OR REDUCING PRESBYOPIA

RELATED APPLICATIONS

This application is a continuation-in-part of U.S. patent application Ser. No. 12/785,734, filed on May 24, 2010, which claims the benefit of U.S. Provisional Application No. 61/180,521, filed on May 22, 2009, and also claims the benefit of U.S. Provisional Application No. 61/291,206, filed on Dec. 30, 2009, the entire content of each of which is hereby incorporated by reference herein.

BACKGROUND

1. Technical Field Text

This application relates to the use of one or more parasympathomimetic drugs or a cholinesterase inhibitor in combination with one or more alpha agonists or antagonist to create optically beneficial miosis to, for example, temporarily treat presbyopia.

2. Background Information

Presbyopia is typically age-related eye deterioration. Young, properly functioning, eyes are able to see at near distances, an ability that deteriorates as one ages. Presbyopia normally develops as a person ages, and is associated with a natural progressive loss of accommodation. A presbyopic eye loses the ability to rapidly and easily focus on objects at near distances. Presbyopia progresses over the lifetime of an individual, usually becoming noticeable after the age of 45 years. By the age of 65 years, the crystalline lens has often lost almost all elastic properties and has only limited ability to change shape.

Use of over the counter reading glasses is a very common way of addressing the vision problems associated with presbyopia. Reading glasses allow the eye to focus on near objects and maintain a clear image. This approach is similar to that of treating hyperopia, or farsightedness.

Many presbyopes are also prescribed bi-focal eyeglasses, where one portion of the lens is corrected for distance vision and another portion of the lens is corrected for near vision. When peering down through the bifocals, the individual looks through the portion of the lens corrected for near vision. When viewing distant objects, the individual looks higher, through the portion of the bi-focals corrected for distance vision. Contact lenses and intra-ocular lenses (IOLs) have also been used to treat presbyopia, for example, by relying on monovision (where one eye is corrected for distance-vision, while the other eye is corrected for near-vision) or bilateral correction with either bi-focal or multi-focal lenses. Laser ablation has also been used to treat presbyopia. All these procedures seek to correct the problem for long term purposes using drastic steps (surgery, laser ablation, etc) or require wearing corrective lenses.

Thus, there remains a need for new ways of ameliorating or reducing presbyopia for patients that do not wish to undergo surgery (IOLs, laser ablation, etc.) or use corrective glasses. For people who use corrective lenses, there remains a need to temporarily treat presbyopia without the use of corrective lenses.

DESCRIPTION OF FIGURES

FIG. 2 shows the average change in visual acuity at 1, 2, 4, 8, and 10 hours after administration for the active drug and placebo arms. The solid squares represent the average change in visual acuity for the active drug arm whereas the solid triangles represent the average change in visual acuity for the placebo arm.

BRIEF SUMMARY

Figure 1:
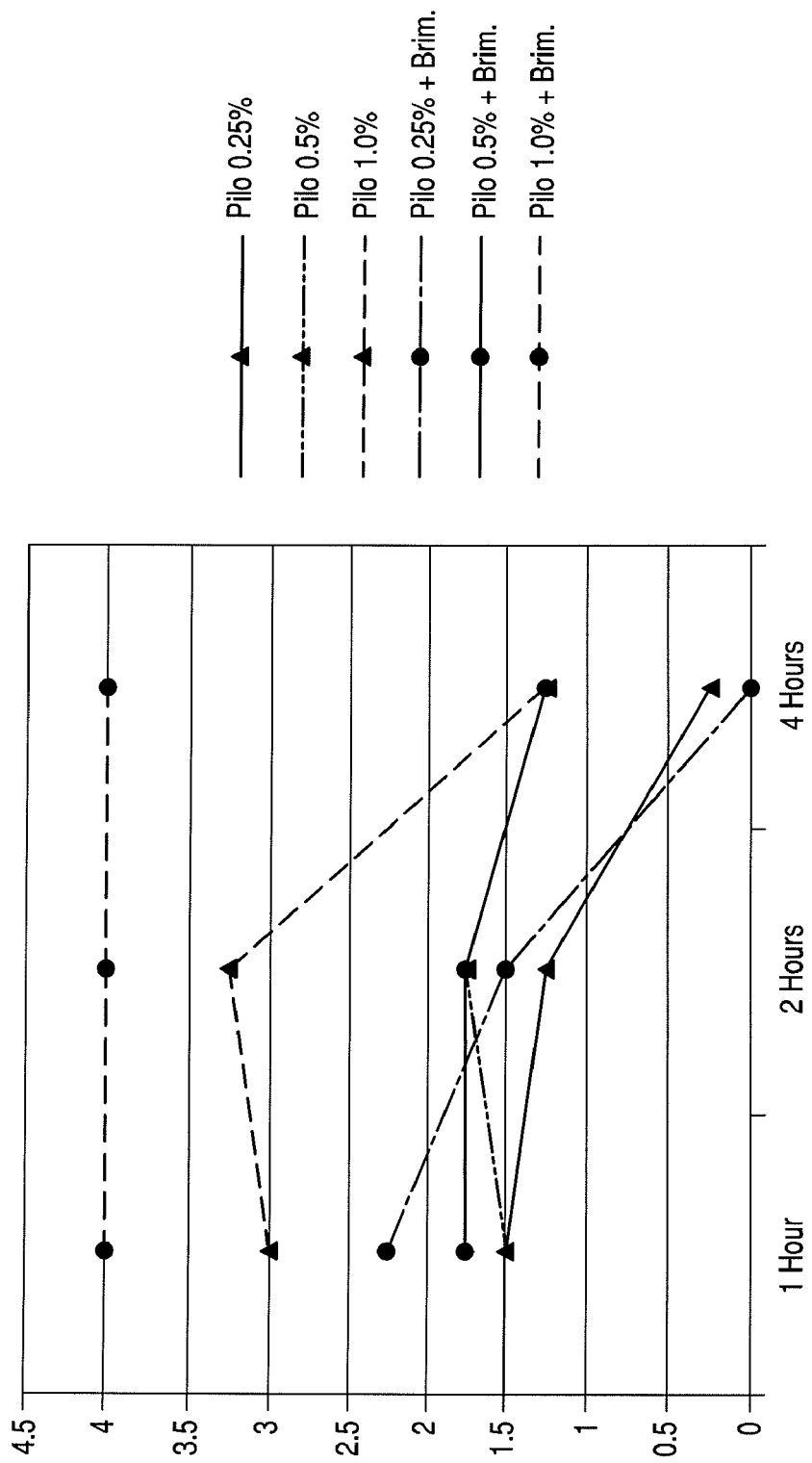
FIG. 1 shows change in visual acuity at 1 hr, 2 hrs, and 4 hrs after administration of 0.25% pilocarpine alone, 0.5% pilocarpine alone, 1.0% pilocarpine alone, 0.25% pilocarpine combined with 0.2% brimonidine, 0.5%, pilocarpine combined with 0.2% brimonidine, or 1.0% pilocarpine combined with 0.2% brimonidine

This application relates to a pharmaceutical preparation comprising one or more parasympathomimetic drugs or cholinesterase inhibitors and one or more alpha agonists or antagonists. In one embodiment, an ophthalmic topical preparation is provided, comprising a therapeutically effective amount of one or more parasympathomimetic drugs or one or more cholinesterase inhibitors, or their pharmaceutically acceptable salts, and one or more alpha agonists or antagonists, or their pharmaceutically acceptable salts. The invention further provides for a method for ameliorating or reducing presbyopia of a patient having an eye, comprising administering to the eye a therapeutically effective amount of an ophthalmic preparation comprising one or more parasympathomimetic drugs or one or more cholinesterase inhibitors, or their pharmaceutically acceptable salts, and one or more alpha agonists or antagonists, or their pharmaceutically acceptable salts. The invention also provides for a method of producing ocular miosis in a subject which comprises administering to the subject an amount of a preparation comprising one or more parasympathomimetic drugs or one or more cholinesterase inhibitors, or their pharmaceutically acceptable salts, and one or more alpha agonists or antagonists, or their pharmaceutically acceptable salts, effective to produce ocular miosis.

In some embodiments, the one or more parasympathomimetic drugs is pilocarpine, or carbachol, or their pharmaceutically acceptable salts. In a further embodiment, the one or more alpha agonists is brimonidine, or a pharmaceutically acceptable salt thereof.

In some embodiments, the one or more cholinesterase inhibitor is an organophosphate such as metrifonate, a carbamate such as physostigmine (also known as eserine), neostigmine (also known as prostigmine), pyridostigmine, ambenonium, demarcarium, or rivastigmine; a phenanthrene derivative such as galantamine; a piperidine compound such as donepezil, tacrine (also known as tetrahydroaminoacridine (THA')), edrophonium, huperzine A, or ladostigil. In another embodiment, the cholinesterase inhibitor may be diisopropyl fluorophosphate or DFP (Floropryl). In other embodiments, the one or more cholinesterase inhibitors is phospholine iodide (also known as echothiophate) or physostigmine, or its pharmaceutically acceptable salt. In certain embodiments, the one or more alpha antagonists is doxazosin, silodosin, prazosin, tamsulosin, alfuzosin, terazosin, trimazosin, phenoxybenzamine, or phentolamine, or a pharmaceutically acceptable salt thereof.

In some embodiments, brimonidine, or a pharmaceutically acceptable salt thereof, is present in an amount less than about 0.2%. In other exemplary embodiments, the one or more parasympathomimetic drugs is pilocarpine, or its pharmaceutically acceptable salt, which is present in the preparation in an amount less than about 0.5%. In further exemplary embodiments, the one or more parasympathomimetic drugs is pilocarpine, or its pharmaceutically acceptable salt, which is present in the preparation in an amount of less than about 0.1%.

In some further embodiments, the one or more parasympathomimetic drugs is carbachol, or its pharmaceutically acceptable salt, which is present in the preparation in an amount of about 5%. In certain embodiments, the one or more parasympathomimetic drugs is carbachol, or its pharmaceutically acceptable salt, which is present in the preparation in an amount of no more than 0.001%.

In some further embodiments, the one or more alpha antagonist is phentolamine, or its pharmaceutically acceptable salt, which is present in the preparation in an amount of no more than 2%. In certain embodiments, the one or more alpha antagonist is phentolamine, or its pharmaceutically acceptable salt, which is present in the preparation in an amount of no more than 0.005%.

DETAILED DESCRIPTION OF THE EMBODIMENTS

This application relates to a pharmaceutical preparation comprising one or more parasympathomimetic drugs and one or more alpha agonists. In one embodiment, the one or more parasympathomimetic drug is pilocarpine. In another embodiment, one or more parasympathomimetic drug is carbachol. In further embodiments, the one or more parasympathomimetic drugs are pilocarpine and carbachol. In certain embodiments, the one or more alpha agonists is brimonidine, or a pharmaceutically acceptable salt thereof. The ophthalmic preparation may be administered to a subject suffering from presbyopia as often as needed to cause miosis sufficient to temporarily treat, ameliorate, or reduce presbyopia. Thus, the invention further provides a method for temporarily treating, ameliorating, or reducing presbyopia by inducing miosis.

The invention also relates to a method for ameliorating or reducing presbyopia of a patient having an eye, comprising administering to said eye a therapeutically effective amount of an ophthalmic preparation comprising one or more parasympathomimetic drugs or cholinesterase inhibitors, or pharmaceutically acceptable salts thereof, and one or more alpha agonists or antagonists, or pharmaceutically acceptable salts thereof.

In one embodiment, the invention is directed to a method of reducing or eliminating dimness of vision of a patient having an eye comprising administering to said eye a therapeutically effective amount of an ophthalmic preparation comprising one or more parasympathomimetic drugs or cholinesterase inhibitors, or pharmaceutically acceptable salts thereof, and one or more alpha agonists or antagonists, or pharmaceutically acceptable salts thereof.

In some embodiments, the invention is directed to a method of improving focus and/or correcting refractive errors of a patient having an eye comprising administering to said eye a therapeutically effective amount of an ophthalmic preparation comprising one or more parasympathomimetic drugs or cholinesterase inhibitors, or pharmaceutically acceptable salts thereof, and one or more alpha agonists or antagonists, or pharmaceutically acceptable salts thereof. Although brimonidine is not ordinarily used to constrict the pupil, and thus enhance visual acuity, applicants discovered that it potentiates the effect of pilocarpine on the pupil. Thus, an embodiment of the present application is a method for ameliorating or reducing presbyopia of a patient by applying to the one or both eyes of the patient a therapeutically effective amount of pilocarpine, or pharmaceutically acceptable salts thereof, and an effective amount of brimonidine, or pharmaceutically acceptable salts thereof. Another embodiment of the present application is a method for ameliorating or reducing presbyopia of a patient by applying to the one or both eyes of the patient a therapeutically effective amount of carbachol, or pharmaceutically acceptable salts thereof, and an effective amount of brimonidine, or pharmaceutically acceptable salts thereof. In some embodiments, the two drugs are administered as a single combined ophthalmic preparation. In another embodiment, the two drugs are formulated or as two separate ophthalmic preparations and applied to the eye successively or simultaneously.

Brimonidine should also potentiate the effect on the pupil of other parasympathomimetic drugs such as acetylcholine, muscarine, nicotine, suxamethonium, bethanechol, carbachol, methacholine, phenylpropanolamine, amphetamine, ephedrine, phentolamine, and fenfluramine) as well as cholinesterase inhibitors such as metrifonate, neostigmine (prostigmine), pyridostigmine, ambenonium, demarcarium, rivastigmine, galantamine, donepezil, tacrine (tetrahydroaminoacridine), edrophonium, huperzine A, ladostigil, diisopropyl fluorophosphate (Floropryl), phospholine iodide (echothiophate) or physostigimine (eserine).

It may also be beneficial to administer the pharmaceutical preparations described herein to only a single eye of a patient. In some instances, blurring of distance vision (a result of accommodative focus) and dimness of vision (a result of pupil constriction) may occur when the compositions are administered to both eyes of a patient. When applied to only a single eye, the benefits of improvement in presbyopia are obtained with diminished or complete relief of blurring and dimness. Without being bound to any particular theory, it is believed that a patient's brain compensates between the treated and untreated eyes thereby reducing the undesired effects. The combination of a constricted pupil with its increased depth of field in the treated eye and normal distance vision and brightness in the untreated eye will cause the brain to ignore any monocular blur at distance or near vision.

As used herein, the term "parasympathomimetic agent or drug" is intended to include to any cholinergic drug that enhances the effects mediated by acetylcholine in the central nervous system, the peripheral nervous system, or both. Examples of these so-called acetylcholine receptor agonists suitable for the preparations and methods of the present invention include acetylcholine, muscarine, pilocarpine, nicotine, suxamethonium, bethanechol, carbachol, methacholine, phenylpropanolamine, amphetamine, ephedrine, phentolamine, and fenfluramine.

As used herein, the term "alpha agonist" refers to compounds that preferentially stimulate alpha (both alpha1 and alpha2) adrenoceptors. Examples of alpha androgenic agonist suitable for the preparations and methods of the present invention include amiloride, apraclonidine, brimonidine, clonidine (and its derivatives such as p-chloro and amino derivatives), detomidine, dexmedetomidine, dipivalylepinephrine, epinephrine, guanabenz, guanfacine, isoproterenol, medetomidine, metaproterenol, mephentermine, methoxamine, methyldopa, naphazoline, norepinephrine, phenylephrine, rilmenidine, salbutamol, terbutaline, tetrahydrozoline, and xylazine and their pharmaceutically acceptable salts and prodrugs.

In the subject invention a "therapeutically effective amount" is any amount of the two or more active ingredients present in the preparation of the present invention which, when administered to a subject suffering from presbyopia are effective to cause miosis sufficient to temporarily reduce, ameliorate, or treat presbyopia such that the near vision of the treated eye is temporarily restored partially or completely. A complete restoration of the near vision should be sufficient to allow the person to read a Times New Roman font of size 12 without any other aid. A partial restoration of near vision will allow the treated eye to see with decreased blurriness. Thus, a therapeutically effective amount refers to the amount of a therapeutic preparation that reduces the extent of presbyopia by at least 10%, at least 20%, at least 30%, at least 40%, at least 50%, at least 60%, at least 70%, at least 80%, at least 90%, or at least 100%. For certain embodiments, the amount of the ophthalmic preparation comprising the one or more parasympathomimetic drugs and the one or more alpha agonists is effective to ameliorate or reduce presbyopia for about 12 hours, 11 hours, 10 hours, 9 hours, 8 hours, 7 hours, 6 hours, 5 hours, 4 hours, 3 hours, 2 hours or 1 hour. The extent of presbyopia can be determined by any method known in the art for ophthalmic examination.

The terms "ameliorate, ameliorating, and amelioration," as used herein, are intended to refer to a decrease in the severity of presbyopia. The amelioration may be complete, e.g., the total absence of presbyopia. The amelioration may also be partial, such that the amount of presbyopia is less than that which would have been present without the present invention. For example, the extent of presbyopia-using the methods of the present invention may be at least 10%, at least 20%, at least 30%, at least 40%, at least 50%, at least 60%, at least 70%, at least 80%, at least 90%, or at least 100% less than the amount of presbyopia that would have been present without the present invention.

The pharmaceutical preparations of the present invention are adapted for topical administration to the eye in the form of solutions, suspensions, ointments, or creams. The ophthalmic pharmaceutical preparation of the present invention may be used in the form of an eyewash, ophthalmic solution (e.g., eye drop), or ophthalmic ointment.

The ophthalmic pharmaceutical preparation of the present invention may be prepared using commonly used pharmaceutically-acceptable carriers in such a manner of mixing them with an effective amount of the one or more parasympathomimetic drugs and one or more alpha agonists to suit the desired formulation. The carriers used for ophthalmic solutions and eyewashes include any one of those which are commonly used therefor, usually, purified water. The ophthalmic pharmaceutical preparation of the present invention can be previously prepared into a solution form or processed into a solid preparation using lyophilization method, etc., to be used in the desired preparation, for example, dissolving the solid preparation in the desired liquid carrier. Examples of such a solid preparation include tablets, granules, and powders. These ophthalmic pharmaceutical preparations can be prepared in accordance with conventional methods and should preferably be sterilized before use by conventional methods using membrane filters, autoclaves, etc. The ophthalmic preparations may comprise saccharides such as glucose and maltose; sugar alcohols such as mannitol and sorbitol; electrolytes such as sodium chloride, sodium hydrogenphosphate, potassium chloride, magnesium sulfate, and calcium chloride; amino acids such as glycine and alanine; vitamins and derivatives thereof such as thiamine hydrochloride, sodium riboflavin phosphate, pyridoxine hydrochloride, nicotinamide, folic acid, biotin, vitamin A, L-ascorbic acid, and α-glycosyl-L-ascorbic acid, which all can be used in an appropriate combination. Particularly, in the case of the ophthalmic pharmaceutical preparation of the present invention is in the form of an ophthalmic solution, the combination use of the one or more parasympathomimetic drugs and one or more alpha agonists as an effective ingredient and one or more other saccharides selected from monosaccharides such as glucose and fructose, disaccharides such as maltose, and oligosaccharides higher than maltotriose may stably exert a satisfactory therapeutic effect. In addition, viscosity-imparting agents such as methyl cellulose, carboxy methyl cellulose, chondroitin sulfate, polyvinyl alcohol, and pullulan; solubilizers such as polysorbate 80 may be used in the preparations.

In some embodiments, the composition of the present invention may be formulated as a powder substantially free of water wherein the composition is reconstituted to a solution, a suspension, an ointment, or a cream just prior to use by the patient or a treating physician. Some embodiments may contain the active ingredients and other excipients but are free of water. Of course, the active ingredient and/or one or more excipient may be hygroscopic and as such may contain small amount of water. Some embodiments contain no more than 0.1%, 0.5%, 1%, 2%, 3%, 4%, 5%, 6%, 7%, 8%, 9%, or 10% by weight of water in the composition.

The preparations may contain from about 0.0001% to about 5% for each of the one or more parasympathomimetic drugs and the one or more alpha agonists.

In one embodiment, the preparation comprises brimonidine and a parasympathomimetic drug. In another embodiment, the parasympathomimetic drug is pilocarpine. In a further embodiment, the parasympathomimetic drug is carbachol. In another embodiment, the parasympathomimetic agent is phentermine.

The one or more parasympathomimetic drugs and the one or more alpha agonists may be present in the pharmaceutical preparation as a pharmaceutically acceptable addition salt. Pharmaceutically acceptable salts are well known in the art and refer to the relatively non-toxic, inorganic and organic acid addition salts of the compound of the present invention. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

In certain embodiments, at least one of the drugs is present in an amount lower than 75% of its effective dose for the purpose for which it is used when administered alone. For example, when pilocarpine is the drug which may be present in an amount lower than 75% of its dosage when used alone, then pilocarpine may be present in the preparation at more than about 3%.

When the alpha2 agonist present in the preparation is brimonidine, some embodiments may include about 0.3% or less, no more than 0.25%, no more than 0.2%, no more than 0.19%, no more than 0.18%, no more than 0.17%, no more than 0.16%, no more than 0.15%, no more than 0.14%, no more than 0.13%, no more than 0.12%, no more than 0.11%, or no more than 0.1% brimonidine or its pharmaceutically acceptable salt.

When the alpha2 agonist present in the preparation is naphazoline, some embodiments may include about 0.2% or less, no more than 0.15%, no more than 0.125%, no more than 0.12%, no more than 0.11%, no more than 0.10%, no more than 0.09%, no more than 0.08%, no more than 0.07%, no more than 0.06%, no more than 0.05% naphazoline or its pharmaceutically acceptable salt. In some embodiments containing pilocarpine, or a pharmaceutically acceptable salt thereof, as the parasympathomimetic drug, the formulations may contain about 3% or less, no more than 2.8%, no more than 2.6%, no more than 2.5%, no more than 2.3%, no more than 2.0%, no more than 1.8%, no more than 1.6%, no more than 1.5%, no more than 1.2%, no more than 1%, no more than 0.9%, no more than 0.8%, no more than 0.7%, no more than 0.6%, no more than 0.5%, no more than 0.4%, no more than 0.3%, no more than 0.275%, no more than 0.25%, no more than 0.225%, no more than 0.2%, no more than 0.175%, no more than 0.15%, no more than 0.125%, no more than 0.1%, no more than 0.09%, no more than 0.08%, no more than 0.07%, no more than 0.06%, no more than 0.05%, no more than 0.04%, no more than 0.03%, no more than 0.02%, no more than 0.01%, no more than 0.005%, no more than 0.0025%, no more than 0.00125%, or no more than 0.001% of pilocarpine or its pharmaceutically acceptable salt.

When the parasympathomimetic drug present in the formulation is carbachol, or its pharmaceutically acceptable salt, some embodiments may contain about 5% or less, no more than 4.5%, no more than 4%, no more than 3.5%, no more than 3%, no more than 2.75%, no more than 2.5%, no more than 2.25%, no more than 2%, no more than 1.75%, no more than 1.5%, no more than 1.25%, no more than 1%, no more than 0.75%, no more than 0.5%, no more than 0.4%, no more than 0.3%, no more than 0.2%, or no more than 0.1% carbachol or its pharmaceutically acceptable salt.

Certain embodiments may contain phentolamine, or a pharmaceutically acceptable salt thereof, as the alpha antagonist. In those embodiments, the preparation may contain about 5% or less, no more than 4%, no more than 3.5%, no more than 3%, no more than 2.5%, no more than 2%, no more than 1.8%, no more than 1.6%, no more than 1.4%, no more than 1.2%, no more than 1%, no more than 0.9%, no more than 0.8%, no more than 0.7%, no more than 0.6%, no more than 0.5%, no more than 0.4%, no more than 0.3%, no more than 0.275%, no more than 0.25%, no more than 0.225%, no more than 0.2%, no more than 0.175%, no more than 0.15%, no more than 0.125%, no more than 0.1%, no more than 0.09%, no more than 0.08%, no more than 0.07%, no more than 0.06%, no more than 0.05%, no more than 0.04%, no more than 0.03%, no more than 0.02%, no more than 0.01%, no more than 0.005%, no more than 0.0025%, no more than 0.00125%, or no more than 0.001% of phentolamine or its pharmaceutically acceptable salt.

In some embodiments, the one or more cholinesterase inhibitors is phospholine iodide (echothiophate) or its pharmaceutically acceptable salt, for example iodide salt. In some embodiments, the phospholine iodide is present in the preparation in an amount of about 0.001% to about 1%. Certain embodiments containing phospholine iodide contain no more than about 0.03%, no more than about 0.06%, no more than about 0.125%, or no more than about 0.25% of the cholinesterase inhibitor. In other embodiments, phospholine iodide is present in the preparation in an amount of about 0.001% to about 0.1%. In further embodiments, phospholine iodide is present in the preparation in no more than 0.01, 0.02, 0.03, 0.04, 0.05, 0.06, 0.07, 0.08, 0.09, 0.1, 0.2, 0.3, 0.4, or 0.5%. In one embodiment, the echothiophate salt is an iodide salt present in the preparation in no more than 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, or 0.005%.

In one embodiment, the one or more cholinesterase inhibitors is a physostigmine salt (eserine), for example a salicylate salt, which is present in the preparation in an amount ranging from about 0.01% to about 2%. In further embodiments, physostigmine salicylate is present in the preparation in no more than 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, or 0.005%.

In another embodiment, the one or more cholinesterase inhibitors is rivastigmine salt, for example tartarate salt, which is present in the preparation in an amount ranging from about 0.01% to about 2%. In further embodiments, rivastigmine salt is present in the preparation in no more than 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, or 0.005%.

In a certain embodiment, the one or more cholinesterase inhibitors is donepezil, for example hydrochloride salt, which is present in the preparation in an amount ranging from about 0.01% to about 2%. In further embodiments, donepezil is present in the preparation in no more than 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, or 0.005%. In a further embodiment, the one or more cholinesterase inhibitors, such as donepezil hydrochloride and rivastigmine tartarate, may be present in the preparation in an amount of about 0.001% to about 0.1%. In some embodiments, donepezil hydrochloride or rivastigmine tartarate is present in the preparation in no more than 0.01, 0.02, 0.03, 0.04, 0.05, 0.06, 0.07, 0.08, 0.09, 0.1, 0.2, 0.3, 0.4, or 0.5%.

Unless otherwise specified elsewhere, the "%" in dosages in the preparations are intended to signify weight percentages.

When the "%" of a monomer in a co-polymer is specified, then that percentage is intended to mean mole (or repeat unit) percent. Thus, in copolymers, repeat units of each monomer are counted to calculate the total number of units of each monomer present in the co-polymer. For example, a co-polymer of two monomers containing on average (number average) three units of one monomer (say monomer A) for every seven units of another monomer (say monomer B) is said to contain 30% monomer A and 70% monomer B.

The pharmaceutical preparation which contains the one or more parasympathomimetic drugs and the one or more alpha agonists may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The pharmaceutical preparation may contain a buffering agent to maintain the pH in the therapeutically useful range of about 4.5 to 8.5. In certain embodiments, the pH is adjusted to about 5-8. In other embodiments, the pH is adjusted to about 6-7.5. In other embodiments, the pH is adjusted to about 7.3. Buffering agents used are those known to those skilled in the art, and, while not intending to be limiting, some examples are acetate, borate, carbonate, citrate, and phosphate buffers. In one embodiment of this invention, boric acid is the buffering agent.

The pharmaceutical preparations may contain one or more emulsifiers. As used herein, an "emulsifier" promotes the formation and/or stabilization of an emulsion. Suitable emulsifiers may be natural materials, finely divided solids, or synthetic materials. Natural emulsifying agents may be derived from either animal or vegetable sources. Those from animal sources include gelatin, egg yolk, casein, wool fat, or cholesterol. Those from vegetable sources include acacia, tragacanth, chondrus, or pectin. Vegetable sources specifically from cellulose derivatives include methyl cellulose and carboxymethyl cellulose to increase the viscosity. Finely divided emulsifiers include bentonite, magnesium hydroxide, aluminum hydroxide, or magnesium trisylicate. Synthetic agents include anionic, cationic or nonionic agents. Particularly useful are sodium lauryl sulfate, benzalkonium chloride or polyethylene glycol 400 monostearate, or any combinations thereof.

The pharmaceutical preparations may contain one or more thickeners. As used herein, a "thickener" refers to an agent that makes the preparation of the present invention dense or viscous in consistency. Suitable thickeners that can be used in the context of the present invention include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids, anionic polymers, and their alkali salts and mixtures thereof.

The pharmaceutical preparations may contain one or more solubilizing agents. As used herein, the term "solubilizing agents" refers to those substances that enable solutes to dissolve. Representative examples of solubilizing agents that are usable in the context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEEN® and spans, e.g., TWEEN 80®. Other solubilizers that are usable for the preparations of the present invention are, for example, polyoxyethylene sorbitan fatty acid ester, polyoxyethylene n-alkyl ethers, n-alkyl amine n-oxides, polyoxamers, organic solvents, such as acetone, phospholipids and cyclodextrins.

The pharmaceutical preparation may contain a mucoadhesive. As used herein, the term "mucoadhesive" means a natural or synthetic component, including macromolecules, polymers, and oligomers, or mixtures thereof, that can adhere to a subject's mucous membrane. Adhesion of mucoadhesives to the mucous membrane occurs primarily through noncovalent interactions, such as hydrogen bonding and Van der Waal forces. Examples of mucoadhesives for use in the embodiments disclosed herein include, but are not limited to, Carbopol®, pectin, alginic acid, alginate, chitosan, hyaluronic acid, polysorbates, such as polysorbate-20, -21, -40, -60, -61, -65, -80, -81, -85; poly(ethyleneglycol), such as PEG-7, -14, -16, -18, -55, -90, -100, -135, -180, -4, -240, -6, -8, -9, -10, -12, -20, or -32; oligosaccharides and polysaccharides, such as Tamarind seed polysaccharide, gellan, carrageenan, xanthan gum, gum Arabic, and dextran; cellulose esters and cellulose ethers; modified cellulose polymers, such as carboxymethylcellulose, hydroxyethylcellulose, hydroxypropyl methylcellulose, hydroxyethyl ethylcellulose; polyether polymers and oligomers, such as polyoxyethylene; condensation products of poly(ethyleneoxide) with various reactive hydrogen containing compounds having long hydrophobic chains (e.g. aliphatic chains of about 12 to 20 carbon atoms), for example, condensation products of poly(ethylene oxide) with fatty acids, fatty alcohols, fatty amides, polyhydric alcohols; polyether compounds, such as poly(methyl vinyl ether), polyoxypropylene of less than 10 repeating units; polyether compounds, such as block copolymers of ethylene oxide and propylene oxide; mixtures of block copolymers of ethylene oxide and propylene oxide with other excipients, for example poly(vinyl alcohol); polyacrylamide; hydrolyzed polyacrylamide; poly(vinyl pyrrolidone); poly(methacrylic acid); poly (acrylic acid) or crosslinked polyacrylic acid, such as Carbomer®, i.e., a homopolymer of acrylic acid crosslinked with either an allyl ether of pentaerythritol, an allyl ether of sucrose, or an allyl ether of propylene. In certain embodiments the mucoadhesive is a polysaccharide. One polysaccharide which is particularly useful as a mucoadhesive in the embodiments disclosed herein is Tamarind seed polysaccharide, which is a galactoxyloglucan that is extracted from the seed kernel of Tamarindus Indica, and can be purchased from TCI America of Portland, Oreg.

The pharmaceutical preparations may contain a tonicity agent to adjust the preparation to the desired isotonic range. Tonicity agents are known to those skilled in the ophthalmic art, and, while not intending to be limiting, some examples include glycerin, mannitol, sorbitol, sodium chloride, and other electrolytes. In one embodiment, the tonicity agent is glycerin. In another embodiment, the tonicity agent is a chloride salt. In some embodiments, the ionic content adjusted to about 0.5% to about 1.8%, expressed as sodium chloride equivalents. In these embodiments, the preparation may, in addition to tonicity adjusting ingredients, comprise an ophthalmically acceptable, water-soluble, non-ionic synthetic polymer having a molecular weight within the range of 300 to 250,000, and a non-charged, non-ionic tonicity adjusting agent.

The exact percentage of the non-ionic synthetic polymer used in the solution will depend on the molecular weight of the selected polymer. However, it is intended that, absent the presence of additional viscosity building agents, the ophthalmic solution will generally have a viscosity between about 1 to about 10 cps. In certain embodiments, the ophthalmic solution has a viscosity of about 2 cps to about 8 cps at 23° C. For example, polyvinyl alcohol and polyethylene glycol are among those non-ionic polymeric substances that may be incorporated into the preparations of the present invention. When polyvinyl alcohol is added to the solution, it will be present in a concentration of from about 0.1% to about 5%, or even from about 0.25% to about 2%, whereas when polyethylene glycol is used it will comprise from about 0.25% to about 3% of the solution. Such polymers are commercially available and their composition well known to those skilled in the art.

The pharmaceutical preparation may contain a preservative. Preservatives are used to prevent bacterial contamination in multiple-use ophthalmic preparations, and, while not intending to be limiting, examples include benzalkonium chloride, stabilized oxychloro complexes (otherwise known as Purite®), phenylmercuric acetate, chlorobutanol, benzyl alcohol, parabens, and thimerosal. In some embodiments, the preservative is Purite®.

The pharmaceutical preparation may contain a chelating agent to enhance preservative effectiveness. Suitable chelating agents are those known in the art, and, while not intending to be limiting, edetate salts like edetate disodium, edetate calcium disodium, edetate sodium, edetate trisodium, and edetate dipotassium are examples of useful preservatives.

The pharmaceutical preparations of the present invention may be formulated as sustained release formulation wherein the active ingredients are released over several hours. For example, a stable fluid preparation for the sustained release preparation may comprise a synthetic polymer comprising both hydrophilic and hydrophobic components such that the active ingredients become encapsulated or dispersed in micellar droplets.

The polymer may be a homopolymer of a monomer containing a pendent hydrophilic group such as an acid group, or it may be a copolymer of different monomers, some or all of which contain pendent hydrophilic groups such as an acid group. The monomers may be vinyl monomers. The co-polymer may contain about 10% or more of the monomer containing the hydrophilic pendent group. In one embodiment, more than 25% by weight of the monomers contain a hydrophilic pendent group. In another embodiment, more than 40% by weight of the monomers contain a hydrophilic pendent group. In certain embodiments, 10-100% by weight of the monomers contain a hydrophilic pendent group and 0-90% of monomers are hydrophobic monomers. In other embodiments, 25-100% by weight of the monomers contain a hydrophilic pendent group and 0-75% of monomers are hydrophobic monomers. In further embodiments, 40-100% by weight of the monomers contain a hydrophilic pendent group, and 0-60% of monomers are hydrophobic monomers.

The particular choice of monomers will be made having regard to the desired solubility or dispersability of the polymer, the desired release pattern and other properties required of the particular formulation. Although the polymers used in the present preparations are generally free of cross-linking agent and comprise both hydrophilic monomers and hydrophobic monomers, cross-linking may be used as additional control of the properties of the polymer. For instance, by including a small amount of a trifunctional cross-linkable monomer may be added to the monomer mixture from which the polymer is made. The amount of cross-linkable monomer is generally small, for instance 1-15% by weight, or 1-10% by weight. In certain embodiments, the polymers may comprise from 10 to 75% hydrophilic monomers and from 20 to 80% hydrophobic monomers. In other embodiments, the polymers may comprise from 10 to 55% hydrophilic monomers and from 30 to 60% hydrophobic monomers.

Suitable hydrophilic monomers include monomeric acids, such as acrylic, methacrylic, itaconic, crotonic, vinyl sulfonic, maleic, angelic, oleic, or .alpha.-chloro-acrylic acid or sulfoethyl-methacrylate and vinyl pyrrolidone. Naturally dicarboxylic acids such as maleic acid may be introduced in the form of the anhydride.

Suitable hydrophobic monomers include alkyl acrylates, alkyl methacrylates, vinyl ethers, acrylonitrile, hydroxymethacrylate, styrene and vinyl acetate. The alkyl groups in alkylacrylates and alkylmethacrylates usually contain 1 to 4 carbon atoms, e.g. ethyl, methyl or butyl, but longer chain groups containing up to, say, 18 carbon atoms, e.g., lauryl, can be used. In particular when hydrophobic monomer is present, at least part of it can be a plasticizing monomer in a proportion of 5% to 20% by weight. In certain embodiments, the plasticizing monomer makes about 10% of the polymer. Suitable plasticizing monomers are long chain esters of acrylic or methacrylic acid, e.g. ethyl hexyl acrylate.

In certain embodiments, the polymer is a copolymer of hydrophilic monomers selected from acrylic acid, vinyl pyrrolidone, methacrylic acid and maleic anhydride and hydrophobic monomers selected from methyl methacrylate, butyl methacrylate, lauryl methacrylate, methylacrylate, 2-ethylhexylacrylate and styrene. In another embodiment, the polymer may include acrylic acid with or without vinyl pyrrolidone. In certain embodiments, the polymer may contain from 20 to 55% acrylic acid.

EXAMPLE 1

| Ophthalmic solution In 100 ml | |
|---|---|
| Ingredient | Amount |
| Brimonidine or its pharmaceutically acceptable salt | 0.1, 0.15, 0.2, or 0.25 g |
| carbachol or its pharmaceutically acceptable salt | 5, 4.5, 4, 3.5, 3, 2.75, 2.5, 2.25, 2, 1.75, 1.5, 1.25, 1, 0.75, or 0.5 g |
| Sodium chloride | 0.4 g |
| D-Glucose | 0.04 g |
| Sterilized refined water | Balance |
| Total | 100 ml |

The above ingredients are prepared in a usual manner into a sterilized preparation as an ophthalmic solution, adjusting, if necessary, the pH to about 7.3. This example provides for sixty different ophthalmic preparations.

EXAMPLE 2

| Ophthalmic solution In 100 ml | |
|---|---|
| Ingredient | Amount |
| Brimonidine or its pharmaceutically acceptable salt | 0.1, 0.15, 0.2, or 0.25 g |
| pilocarpine or its pharmaceutically acceptable salt | 3, 2.8, 2.6, 2.5, 2.3, 2.0, 1.8, 1.6, 1.5, 1.2, 1, 0.9, 0.8, 0.7, 0.6, 0.5, 0.4, 0.3, 0.2, or 0.1 g |
| Sodium chloride | 0.4 g |
| D-Glucose | 0.04 g |
| Sterilized refined water | Balance |
| Total | 100 ml |

The above ingredients are prepared in a usual manner into a sterilized preparation as an ophthalmic solution, adjusting, if necessary, the pH to 7.3 using a buffer solution. This example provides for eighty different ophthalmic preparations.

EXAMPLE 3

| Ophthalmic solution In 100 ml | |
|---|---|
| Ingredient | Amount |
| Brimonidine or its pharmaceutically acceptable salt | 0.1, 0.15, 0.2, or 0.25 g |
| phentolamine or its pharmaceutically acceptable salt | 0.1, 0.2, or 0.4 g |
| Sodium chloride | 0.4 g |
| D-Glucose | 0.04 g |
| Sterilized refined water | Balance |
| Total | 100 ml |

The above ingredients are prepared in a usual manner into a sterilized preparation as an ophthalmic solution, adjusting, if necessary, the pH to 7.3 using a buffer solution. This example provides for twelve different ophthalmic preparations.

EXAMPLE 4

The effect of pilocarpine alone or in combination with brimonidine on near visual acuity (VA) for patients suffering from presbyopia was evaluated. Initially, 10 patients were selected for preliminary evaluation. Each patient was administered with one drop of a formulation containing 0.25%, 0.5%, or 1.0% pilocarpine with or without one drop of a formulation containing 0.2% brimonidine. Thus, the following six dosages were initially tested:

1. 0.25% pilocarpine,
2. 0.5% pilocarpine,
3. 1.0% pilocarpine,
4. 0.25% pilocarpine and 0.2% brimonidine,
5. 0.5% pilocarpine and 0.2% brimonidine, and
6. 1.0% pilocarpine and 0.2% brimonidine.

FIG. 1 shows change in visual acuity at 1 hr, 2 hrs, and 4 hrs after administration of one of the six dosages described above. Table 1 shows the effect of the six formulations on pupil diameter and visual acuity of the six formulations. Although some patients displayed burning symptoms on their eyes, it should be noted that the formulations were not optimized for patient comfort. All six dosages provided some (varying) initial improvement in visual acuity. However, the effect of formulations containing pilocarpine alone appears to wear out fairly quickly whereas it takes longer time for effects of formulations containing both drugs to wear out.

To further understand the effectiveness of the formulation containing 0.5% pilocarpine and 0.2% brimonidine, applicant conducted a double-blind, randomized clinical trial. Forty patients suffering from presbyopia were recruited. The patients were randomly divided into two arms: the active drug arm and the placebo arm. Prior to receiving the treatment, the visual acuity of each patient was measured. On day 1 of the trial, patients enrolled in the active drug arm received one drop containing 0.5%, pilocarpine and one drop containing 0.2% brimonidine. The skilled artisan would recognize that the two drugs can be formulated as a composition containing both drugs and applied the desired number of drops of the composition to the eye such that both drugs are delivered to the eye simultaneously. Patients enrolled in placebo arm received two drop of placebo. Patients' responses to the treatment were examined by measuring the visual acuity of each patient at 1, 2, 4, 8, and 10 hrs after treatment. The treatment was repeated for seven days, each time administering the specified amount and examining patients' responses at 1, 2, 4, 8, and 10 hrs after treatment by measuring their visual acuity. Table 2 lists patients' visual acuities, measured prior to the treatment and at 1, 2, 4, 8, and 10 hrs after treatment for days 1 through 7. Although some patients displayed burning symptoms on their eyes, it should be noted that the formulations were not optimized for patient comfort.

FIG. 2 shows the average change in visual acuity at 1, 2, 4, 8, and 10 hours after administration for the active drug and placebo arms. The solid squares represent the average change in visual acuity for the active drug arm whereas the solid triangles represent the average change in visual acuity for the placebo arm. As can be seen from the data, there is a residual effect of the drug eight hours after administration for the active drug arm, allowing patients to read without corrective lenses for several hours.

Having now fully described the invention, it will be understood by those of ordinary skill in the art that the same can be performed within a wide and equivalent range of conditions, formulations and other parameters without affecting the scope of the invention or any embodiment thereof.

TABLE 1

| | | | Pre-Treatment | | | | | | | | Pilo Alone | | |
|---|---|---|---|---|---|---|---|---|---|---|---|---|---|
| | | | | | | | | Pupil | | | | 1 hr | |
| | | | Right Eye | | | Left Eye | | | Diam | | Near Va | Pilo | | nVA |
| # | Age | Sex | Sph | Cyl | Axis | Sph | Cyl | Axis | O.D. | O.S. | (j) | [%] | Pupil | (J) |
| 1 | 47 | M | 0 | 0 | 0 | 0 | 0 | 0 | 4.5 | 4.5 | 3 | 0.25 | 3.5 | 2 |
| 2 | 54 | M | 0 | 0 | 0 | 0 | 0 | 0 | 5.5 | 5.4 | 5 | 0.25 | 2.5 | 3 |

TABLE 1-continued

| # | Age | Sex | | | | | | | | | | | |
|---|---|---|---|---|---|---|---|---|---|---|---|---|---|
| 3 | 49 | M | 0 | 0 | 0 | 0 | 0 | 0 | 4 | 4 | 6 | 0.25 | 3.3 | 5 |
| 4 | 54 | F | 0 | −0.5 | 20 | 0.5 | −0.5 | 160 | 3.5 | 3.5 | 8 | 0.25 | 3 | 6 |
| 5 | 53 | F | 0 | 0 | 0 | 0 | 0 | 0 | 4 | 4 | 6 | 0.5 | 2.5 | 3 |
| 6 | 47 | F | 0 | 0 | 0 | 0 | 0 | 0 | 4 | 4.3 | 5 | 0.5 | 3.8 | 3 |
| 7 | 53 | F | 0 | 0 | 0 | 0 | −0.5 | 25 | 3.5 | 3.5 | 6 | 0.5 | 3 | 6 |
| 8 | 52 | F | 0 | 0 | 0 | 0 | 0 | 0 | 5 | 5 | 6 | 0.5 | 3 | 5 |
| 9 | 52 | F | 0 | 0 | 0 | −0.5 | −0.5 | 135 | 4.3 | 3.9 | 5 | 1 | 2.5 | 3 |
| 10 | 53 | F | 0 | 0 | 0 | 0 | 0 | 0 | 3 | 3 | 8 | 1 | 1.5 | 3 |
| 11 | 53 | F | 0 | 0 | 0 | −0.5 | −0.25 | 175 | 4.5 | 4.5 | 5 | 1 | 2.5 | 2 |
| 12 | 52 | F | 0 | 0 | 0 | 0 | 0 | 0 | 4.5 | 4.5 | 10 | 1 | 3 | 8 |

| | Pilo Alone | | | | | Pilo + Brimonidine | | | | | | |
|---|---|---|---|---|---|---|---|---|---|---|---|---|
| | 2 hrs | | 4 hrs | | | 1 hr | | 2 hrs | | 4 hrs | | |
| # | Pupil | nVA (J) | Pupil | nVA (J) | Pilo [%] | Pupil | nVA (J) | Pupil | nVA (J) | Pupil | nVA (J) |
| 1 | 4 | 3 | 4 | 3 | 0.25 | 3 | 2 | 2.5 | 2 | 3.5 | 3 |
| 2 | 3.5 | 3 | 4 | 5 | 0.25 | 3.3 | 3 | 3.5 | 3 | 4 | 5 |
| 3 | 3 | 5 | 4 | 6 | 0.25 | 2.5 | 3 | 3 | 5 | 3.5 | 8 |
| 4 | 3.5 | 6 | 4 | 7 | 0.25 | 2 | 5 | 3 | 6 | 3.5 | 6 |
| 5 | 3 | 5 | 3.3 | 5 | 0.5 | 2 | 3 | 2.5 | 3 | 3.5 | 5 |
| 6 | 4 | 3 | 4 | 3 | 0.5 | 3 | 3 | 3 | 3 | 3.75 | 3 |
| 7 | 2.5 | 5 | 3 | 5 | 0.5 | 2.5 | 5 | 3 | 5 | 3 | 5 |
| 8 | 3.3 | 3 | 4.2 | 5 | 0.5 | 3 | 5 | 3 | 5 | 3 | 5 |
| 9 | 3 | 3 | 4 | 5 | 1 | 3 | 2 | 3 | 3 | 3.5 | 4 |
| 10 | 1.5 | 2 | 2.5 | 5 | 1 | 2 | 3 | 2 | 2 | 2.5 | 3 |
| 11 | 2.5 | 2 | 3 | 3 | 1 | 2 | 2 | 2 | 3 | 2.5 | 2 |
| 12 | 3 | 8 | 4 | 10 | 1 | 3 | 5 | 3 | 4 | 4 | 3 |

TABLE 2

PILOT STUDY - PILOCARPINE 0.5% PLUS BRIMONIDIE 0.2% EYE DROPS VS. PLACEBO TO REDUCE THE NEED FOR READING GLASSES (X7 DAYS)

| | Pre-treatment | | | Day 1 | | | | | Day 2 | | | | |
|---|---|---|---|---|---|---|---|---|---|---|---|---|---|
| | Age | Sex | Near VA (j) | Near VA (J) 1 hr | Near VA (J) 2 hr | Near VA (J) 4 hr | Near VA (J) 8 hr | Near VA (J) 10 hr | Near VA (J) 1 hr | Near VA (J) 2 hr | Near VA (J) 4 hr | Near VA (J) 8 hr | Near VA (J) 10 hr |
| Pilocarpine 0.5% Plus Brimonidine 0.2% Eye Drops | 55 | M | 8 | 3 | 5 | 6 | 8 | 8 | 3 | 3 | 5 | 8 | 8 |
| | 50 | F | 5 | 2 | 2 | 2 | 3 | 5 | 2 | 2 | 2 | 3 | 5 |
| | 55 | F | 8 | 5 | 5 | 6 | 7 | 8 | 4 | 5 | 5 | 6 | 8 |
| | 48 | F | 8 | 3 | 2 | 5 | 8 | 8 | 3 | 3 | 5 | 8 | 8 |
| | 49 | F | 6 | 3 | 5 | 5 | 5 | 6 | 4 | 5 | 5 | 5 | 6 |
| | 48 | M | 3 | 1 | 1 | 1 | 2 | 3 | 1 | 1 | 1 | 1 | 2 |
| | 52 | M | 8 | 5 | 5 | 6 | 8 | 8 | 6 | 6 | 8 | 8 | 8 |
| | 55 | F | 10 | 8 | 8 | 10 | 10 | 10 | 8 | 8 | 10 | 10 | 10 |
| | 47 | M | 6 | 2 | 3 | 5 | 5 | 6 | 2 | 3 | 5 | 5 | 6 |
| | 45 | F | 3 | 1 | 1 | 1 | 2 | 3 | 1 | 1 | 1 | 2 | 3 |
| | 47 | F | 5 | 2 | 2 | 3 | 5 | 5 | 2 | 2 | 3 | 4 | 5 |
| | 54 | M | 8 | 3 | 3 | 5 | 7 | 8 | 3 | 3 | 5 | 5 | 8 |
| | 49 | F | 6 | 4 | 4 | 5 | 6 | 6 | 4 | 5 | 5 | 6 | 6 |
| | 53 | M | 8 | 4 | 4 | 4 | 7 | 8 | 4 | 4 | 5 | 8 | 8 |
| | 53 | M | 7 | 5 | 5 | 6 | 7 | 7 | 5 | 5 | 6 | 7 | 7 |
| | 47 | F | 5 | 2 | 2 | 2 | 3 | 5 | 1 | 2 | 3 | 5 | 5 |
| | 45 | M | 5 | 1 | 1 | 2 | 3 | 5 | 1 | 1 | 2 | 3 | 5 |
| | 48 | M | 5 | 2 | 2 | 3 | 5 | 5 | 2 | 2 | 5 | 5 | 5 |
| | 53 | F | 6 | 2 | 2 | 5 | 6 | 6 | 2 | 2 | 5 | 6 | 6 |
| | 45 | M | 3 | 1 | 1 | 1 | 2 | 3 | 1 | 1 | 1 | 3 | 3 |
| SUM | | | 123 | 59 | 63 | 83 | 109 | 123 | 59 | 64 | 87 | 108 | 122 |
| AVERAGE | | | 6.15 | 2.95 | 3.15 | 4.15 | 5.45 | 6.15 | 2.95 | 3.2 | 4.35 | 5.4 | 6.1 |
| Placebo Eye Drops | 49 | M | 6 | 6 | 6 | 6 | 6 | 6 | 6 | 6 | 6 | 6 | 6 |
| | 51 | M | 5 | 5 | 5 | 5 | 5 | 5 | 5 | 5 | 5 | 5 | 5 |
| | 50 | M | 5 | 5 | 4 | 5 | 5 | 5 | 4 | 5 | 5 | 5 | 5 |
| | 54 | F | 8 | 8 | 8 | 8 | 8 | 9 | 7 | 8 | 8 | 8 | 8 |
| | 49 | F | 5 | 4 | 5 | 5 | 5 | 5 | 4 | 5 | 5 | 5 | 5 |
| | 52 | M | 6 | 6 | 6 | 6 | 6 | 6 | 6 | 6 | 6 | 6 | 6 |
| | 47 | M | 5 | 5 | 5 | 5 | 5 | 5 | 5 | 5 | 5 | 5 | 5 |
| | 45 | F | 3 | 3 | 3 | 3 | 3 | 3 | 2 | 3 | 3 | 3 | 3 |
| | 54 | M | 8 | 8 | 8 | 8 | 8 | 8 | 8 | 8 | 8 | 8 | 8 |
| | 53 | F | 8 | 8 | 8 | 8 | 8 | 8 | 8 | 8 | 8 | 8 | 8 |
| | 49 | F | 6 | 5 | 6 | 6 | 6 | 6 | 6 | 6 | 6 | 6 | 6 |
| | 55 | F | 8 | 6 | 8 | 8 | 8 | 8 | 8 | 8 | 8 | 8 | 8 |

TABLE 2-continued

PILOT STUDY - PILOCARPINE 0.5% PLUS BRIMONIDIE 0.2% EYE DROPS
VS. PLACEBO TO REDUCE THE NEED FOR READING GLASSES (X7 DAYS)

|  | 52 | M | 8 | 8 | 8 | 8 | 8 | 8 | 8 | 8 | 8 | 8 | 8 |
|---|---|---|---|---|---|---|---|---|---|---|---|---|---|
|  | 46 | F | 6 | 5 | 6 | 6 | 6 | 6 | 5 | 5 | 6 | 6 | 6 |
|  | 48 | F | 6 | 6 | 6 | 6 | 6 | 6 | 6 | 6 | 6 | 6 | 6 |
|  | 50 | M | 5 | 5 | 5 | 5 | 5 | 5 | 5 | 5 | 5 | 5 | 5 |
|  | 50 | M | 6 | 6 | 6 | 6 | 6 | 6 | 6 | 6 | 6 | 6 | 6 |
|  | 47 | F | 5 | 3 | 5 | 5 | 5 | 5 | 3 | 3 | 5 | 5 | 5 |
|  | 54 | M | 10 | 10 | 10 | 10 | 10 | 10 | 10 | 10 | 10 | 10 | 10 |
|  | 45 | F | 3 | 2 | 3 | 3 | 3 | 3 | 2 | 3 | 3 | 3 | 3 |
|  | SUM |  | 122 | 113 | 122 | 122 | 122 | 123 | 114 | 119 | 122 | 122 | 122 |
|  | AVERAGE |  | 6.1 | 5.65 | 6.1 | 6.1 | 6.1 | 6.15 | 5.7 | 5.95 | 6.1 | 6.1 | 6.1 |

|  |  |  | Pre-treatment | Day 3 | | | | | Day 4 | | | | |
|---|---|---|---|---|---|---|---|---|---|---|---|---|---|
|  | Age | Sex | Near VA (j) | Near VA (J) 1 hr | Near VA (J) 2 hr | Near VA (J) 4 hr | Near VA (J) 8 hr | Near VA (J) 10 hr | Near VA (J) 1 hr | Near VA (J) 2 hr | Near VA (J) 4 hr | Near VA (J) 8 hr | Near VA (J) 10 hr |
| Pilocarpine 0.5% Plus Brimonidine 0.2% Eye Drops | 55 | M | 8 | 2 | 3 | 5 | 8 | 8 | 2 | 3 | 5 | 8 | 8 |
|  | 50 | F | 5 | 2 | 2 | 2 | 3 | 5 | 2 | 2 | 2 | 3 | 5 |
|  | 55 | F | 8 | 6 | 6 | 6 | 6 | 8 | 6 | 6 | 6 | 6 | 8 |
|  | 48 | F | 8 | 3 | 3 | 5 | 8 | 8 | 3 | 3 | 5 | 8 | 8 |
|  | 49 | F | 6 | 4 | 5 | 5 | 5 | 6 | 4 | 5 | 5 | 6 | 6 |
|  | 48 | M | 3 | 1 | 1 | 1 | 2 | 3 | 1 | 1 | 2 | 2 | 3 |
|  | 52 | M | 8 | 5 | 6 | 8 | 8 | 8 | 5 | 5 | 8 | 8 | 10 |
|  | 55 | F | 10 | 8 | 8 | 10 | 10 | 10 | 8 | 8 | 10 | 10 | 10 |
|  | 47 | M | 6 | 2 | 2 | 3 | 5 | 6 | 2 | 2 | 3 | 5 | 6 |
|  | 45 | F | 3 | 1 | 1 | 1 | 2 | 3 | 1 | 1 | 1 | 2 | 3 |
|  | 47 | F | 5 | 3 | 3 | 3 | 4 | 5 | 2 | 2 | 3 | 4 | 5 |
|  | 54 | M | 8 | 3 | 3 | 5 | 6 | 8 | 3 | 3 | 6 | 6 | 8 |
|  | 49 | F | 6 | 3 | 4 | 4 | 6 | 6 | 3 | 4 | 4 | 5 | 6 |
|  | 53 | M | 8 | 4 | 4 | 6 | 8 | 8 | 4 | 4 | 6 | 8 | 8 |
|  | 53 | M | 7 | 5 | 5 | 6 | 7 | 7 | 5 | 5 | 7 | 7 | 7 |
|  | 47 | F | 5 | 1 | 1 | 3 | 3 | 5 | 1 | 1 | 2 | 5 | 5 |
|  | 45 | M | 5 | 1 | 1 | 2 | 3 | 5 | 1 | 1 | 3 | 3 | 5 |
|  | 48 | M | 5 | 2 | 2 | 3 | 3 | 5 | 2 | 2 | 3 | 5 | 5 |
|  | 53 | F | 6 | 2 | 2 | 5 | 6 | 6 | 2 | 2 | 5 | 6 | 6 |
|  | 45 | M | 3 | 1 | 1 | 1 | 3 | 3 | 1 | 1 | 1 | 2 | 3 |
|  | SUM |  | 123 | 59 | 63 | 84 | 106 | 123 | 58 | 61 | 87 | 109 | 125 |
|  | AVERAGE |  | 6.15 | 2.95 | 3.15 | 4.2 | 5.3 | 6.15 | 2.9 | 3.05 | 4.35 | 5.45 | 6.25 |
| Placebo Eye Drops | 49 | M | 6 | 6 | 6 | 6 | 6 | 6 | 6 | 6 | 6 | 6 | 6 |
|  | 51 | M | 5 | 5 | 5 | 5 | 5 | 5 | 5 | 5 | 5 | 5 | 5 |
|  | 50 | M | 5 | 4 | 5 | 5 | 5 | 5 | 4 | 5 | 5 | 5 | 5 |
|  | 54 | F | 8 | 8 | 8 | 8 | 8 | 8 | 8 | 8 | 8 | 8 | 8 |
|  | 49 | F | 5 | 4 | 5 | 5 | 5 | 5 | 4 | 5 | 5 | 5 | 5 |
|  | 52 | M | 6 | 6 | 6 | 6 | 6 | 6 | 6 | 6 | 6 | 6 | 6 |
|  | 47 | M | 5 | 5 | 5 | 5 | 5 | 5 | 5 | 5 | 5 | 5 | 5 |
|  | 45 | F | 3 | 2 | 3 | 3 | 3 | 3 | 2 | 3 | 3 | 3 | 3 |
|  | 54 | M | 8 | 8 | 8 | 8 | 8 | 8 | 8 | 8 | 8 | 8 | 8 |
|  | 53 | F | 8 | 7 | 8 | 8 | 8 | 8 | 7 | 8 | 8 | 8 | 8 |
|  | 49 | F | 6 | 6 | 6 | 6 | 6 | 6 | 6 | 6 | 6 | 6 | 6 |
|  | 55 | F | 8 | 8 | 8 | 8 | 8 | 8 | 8 | 8 | 8 | 8 | 8 |
|  | 52 | M | 8 | 8 | 8 | 8 | 8 | 8 | 8 | 8 | 8 | 8 | 8 |
|  | 46 | F | 6 | 5 | 6 | 6 | 6 | 6 | 5 | 6 | 6 | 6 | 6 |
|  | 48 | F | 6 | 6 | 6 | 6 | 6 | 6 | 6 | 6 | 6 | 6 | 6 |
|  | 50 | M | 5 | 5 | 5 | 5 | 5 | 5 | 5 | 5 | 5 | 5 | 5 |
|  | 50 | M | 6 | 6 | 6 | 6 | 6 | 6 | 6 | 6 | 6 | 6 | 6 |
|  | 47 | F | 5 | 3 | 5 | 5 | 5 | 5 | 3 | 5 | 5 | 5 | 5 |
|  | 54 | M | 10 | 10 | 10 | 10 | 10 | 10 | 10 | 10 | 10 | 10 | 10 |
|  | 45 | F | 3 | 2 | 3 | 3 | 3 | 3 | 2 | 3 | 3 | 3 | 3 |
|  | SUM |  | 122 | 114 | 122 | 122 | 122 | 122 | 114 | 122 | 122 | 122 | 122 |
|  | AVERAGE |  | 6.1 | 5.7 | 6.1 | 6.1 | 6.1 | 6.1 | 5.7 | 6.1 | 6.1 | 6.1 | 6.1 |

|  |  |  | Pre-treatment | Day 5 | | | | | Day 6 | | | | |
|---|---|---|---|---|---|---|---|---|---|---|---|---|---|
|  | Age | Sex | Near VA (j) | Near VA (J) 1 hr | Near VA (J) 2 hr | Near VA (J) 4 hr | Near VA (J) 8 hr | Near VA (J) 10 hr | Near VA (J) 1 hr | Near VA (J) 2 hr | Near VA (J) 4 hr | Near VA (J) 8 hr | Near VA (J) 10 hr |
| Pilocarpine 0.5% Plus Brimonidine 0.2% Eye Drops | 55 | M | 8 | 3 | 3 | 5 | 8 | 8 | 3 | 3 | 5 | 8 | 8 |
|  | 50 | F | 5 | 2 | 2 | 3 | 3 | 5 | 2 | 2 | 2 | 3 | 5 |
|  | 55 | F | 8 | 6 | 6 | 6 | 6 | 8 | 5 | 5 | 6 | 7 | 8 |
|  | 48 | F | 8 | 3 | 3 | 5 | 8 | 8 | 3 | 3 | 5 | 8 | 8 |
|  | 49 | F | 6 | 4 | 5 | 5 | 6 | 6 | 4 | 5 | 6 | 6 | 6 |
|  | 48 | M | 3 | 1 | 1 | 1 | 2 | 3 | 1 | 1 | 2 | 3 | 3 |

TABLE 2-continued

PILOT STUDY - PILOCARPINE 0.5% PLUS BRIMONIDIE 0.2% EYE DROPS
VS. PLACEBO TO REDUCE THE NEED FOR READING GLASSES (X7 DAYS)

|  | Age | Sex |  |  |  |  |  |  |  |  |  |  |
|---|---|---|---|---|---|---|---|---|---|---|---|---|
|  | 52 | M | 8 | 5 | 8 | 8 | 8 | 8 | 5 | 5 | 7 | 7 | 8 |
|  | 55 | F | 10 | 8 | 8 | 10 | 10 | 10 | 8 | 9 | 10 | 9 | 10 |
|  | 47 | M | 6 | 2 | 2 | 3 | 5 | 6 | 2 | 2 | 3 | 6 | 6 |
|  | 45 | F | 3 | 1 | 1 | 1 | 2 | 3 | 1 | 1 | 1 | 2 | 3 |
|  | 47 | F | 5 | 2 | 2 | 3 | 4 | 5 | 2 | 3 | 3 | 5 | 5 |
|  | 54 | M | 8 | 3 | 3 | 3 | 6 | 8 | 3 | 3 | 5 | 8 | 8 |
|  | 49 | F | 6 | 3 | 3 | 4 | 4 | 6 | 3 | 3 | 4 | 6 | 6 |
|  | 53 | M | 8 | 4 | 4 | 7 | 8 | 8 | 3 | 4 | 7 | 8 | 8 |
|  | 53 | M | 7 | 4 | 4 | 5 | 6 | 7 | 4 | 4 | 6 | 7 | 7 |
|  | 47 | F | 5 | 1 | 1 | 3 | 5 | 5 | 2 | 2 | 3 | 3 | 5 |
|  | 45 | M | 5 | 1 | 1 | 3 | 3 | 5 | 1 | 1 | 2 | 5 | 5 |
|  | 48 | M | 5 | 2 | 2 | 3 | 5 | 5 | 2 | 2 | 3 | 5 | 5 |
|  | 53 | F | 6 | 2 | 2 | 5 | 6 | 6 | 2 | 2 | 5 | 6 | 6 |
|  | 45 | M | 3 | 1 | 1 | 1 | 2 | 3 | 1 | 1 | 1 | 2 | 3 |
|  | SUM |  | 123 | 58 | 62 | 84 | 107 | 123 | 57 | 61 | 86 | 114 | 123 |
|  | AVERAGE |  | 6.15 | 2.9 | 3.1 | 4.2 | 5.35 | 6.15 | 2.85 | 3.05 | 4.3 | 5.7 | 6.15 |
| Placebo | 49 | M | 6 | 6 | 6 | 6 | 6 | 6 | 6 | 6 | 6 | 6 | 6 |
| Eye | 51 | M | 5 | 4 | 5 | 5 | 5 | 5 | 4 | 5 | 5 | 5 | 5 |
| Drops | 50 | M | 5 | 4 | 5 | 5 | 5 | 5 | 4 | 5 | 5 | 5 | 5 |
|  | 54 | F | 8 | 8 | 8 | 8 | 8 | 8 | 8 | 8 | 8 | 8 | 8 |
|  | 49 | F | 5 | 4 | 5 | 5 | 5 | 5 | 4 | 5 | 5 | 5 | 5 |
|  | 52 | M | 6 | 6 | 6 | 6 | 6 | 6 | 6 | 6 | 6 | 6 | 6 |
|  | 47 | M | 5 | 5 | 5 | 5 | 5 | 5 | 5 | 5 | 5 | 5 | 5 |
|  | 45 | F | 3 | 2 | 3 | 3 | 3 | 3 | 3 | 3 | 3 | 3 | 3 |
|  | 54 | M | 8 | 8 | 8 | 8 | 8 | 8 | 8 | 8 | 8 | 8 | 8 |
|  | 53 | F | 8 | 7 | 8 | 8 | 8 | 8 | 7 | 8 | 8 | 8 | 8 |
|  | 49 | F | 6 | 6 | 6 | 6 | 6 | 6 | 6 | 6 | 6 | 6 | 6 |
|  | 55 | F | 8 | 8 | 8 | 8 | 8 | 8 | 8 | 8 | 8 | 8 | 8 |
|  | 52 | M | 8 | 8 | 8 | 8 | 8 | 8 | 8 | 8 | 8 | 8 | 8 |
|  | 46 | F | 6 | 6 | 6 | 6 | 6 | 6 | 5 | 6 | 6 | 6 | 6 |
|  | 48 | F | 6 | 6 | 6 | 6 | 6 | 6 | 5 | 6 | 6 | 6 | 6 |
|  | 50 | M | 5 | 5 | 5 | 5 | 5 | 5 | 5 | 5 | 5 | 5 | 5 |
|  | 50 | M | 6 | 6 | 6 | 6 | 6 | 6 | 6 | 6 | 6 | 6 | 6 |
|  | 47 | F | 5 | 3 | 5 | 5 | 5 | 5 | 3 | 5 | 5 | 5 | 5 |
|  | 54 | M | 10 | 10 | 10 | 10 | 10 | 10 | 10 | 10 | 10 | 10 | 10 |
|  | 45 | F | 3 | 2 | 3 | 3 | 3 | 3 | 2 | 3 | 3 | 3 | 3 |
|  | SUM |  | 122 | 113 | 122 | 122 | 122 | 122 | 113 | 122 | 122 | 122 | 122 |
|  | AVERAGE |  | 6.1 | 5.65 | 6.1 | 6.1 | 6.1 | 6.1 | 5.65 | 6.1 | 6.1 | 6.1 | 6.1 |

|  |  |  | Pre-treatment | Day 7 | | | | | Averages | | | | |
|---|---|---|---|---|---|---|---|---|---|---|---|---|---|
|  |  |  |  |  |  |  |  |  | 1 hr = | 2 hr = | 4 hr = | 8 hr = | 10 hr = |
|  | Age | Sex | Near VA (j) | Near VA (J) 1 hr | Near VA (J) 2 hr | Near VA (J) 4 hr | Near VA (J) 8 hr | Near VA (J) 10 hr | Average Near VA (J) | Average Near VA (J) | Average Near VA (J) | Average Near VA (J) | Average Near VA (J) |
| Pilocarpine | 55 | M | 8 | 2 | 3 | 5 | 8 | 8 | 2.57 | 3.29 | 5.14 | 8 | 8 |
| 0.5% Plus | 50 | F | 5 | 2 | 2 | 2 | 3 | 5 | 2 | 2 | 2.14 | 3 | 5 |
| Brimonidine | 55 | F | 8 | 5 | 6 | 6 | 7 | 8 | 5.29 | 5.57 | 5.86 | 6.43 | 8 |
| 0.2% Eye | 48 | F | 8 | 3 | 3 | 5 | 8 | 8 | 3 | 2.86 | 5 | 8 | 8 |
| Drops | 49 | F | 6 | 4 | 5 | 5 | 6 | 6 | 3.86 | 5 | 5.14 | 5.57 | 6 |
|  | 48 | M | 3 | 1 | 1 | 3 | 3 | 3 | 1 | 1 | 1.57 | 2.14 | 2.86 |
|  | 52 | M | 8 | 5 | 5 | 7 | 8 | 8 | 5.14 | 5.71 | 7.43 | 7.86 | 8.29 |
|  | 55 | F | 10 | 8 | 8 | 9 | 9 | 10 | 8 | 8.14 | 9.86 | 9.71 | 10 |
|  | 47 | M | 6 | 2 | 2 | 3 | 6 | 6 | 2 | 2.29 | 3.57 | 5.29 | 6 |
|  | 45 | F | 3 | 1 | 1 | 1 | 2 | 3 | 1 | 1 | 1 | 2 | 3 |
|  | 47 | F | 5 | 2 | 3 | 3 | 5 | 5 | 2.14 | 2.43 | 3 | 4.43 | 5 |
|  | 54 | M | 8 | 3 | 3 | 6 | 8 | 8 | 3 | 3 | 5 | 6.57 | 8 |
|  | 49 | F | 6 | 3 | 3 | 4 | 6 | 6 | 3.29 | 3.71 | 4.29 | 5.57 | 6 |
|  | 53 | M | 8 | 3 | 4 | 6 | 7 | 8 | 3.71 | 4 | 5.86 | 7.71 | 8 |
|  | 53 | M | 7 | 4 | 4 | 7 | 7 | 7 | 4.57 | 4.57 | 6.14 | 6.86 | 7 |
|  | 47 | F | 5 | 1 | 2 | 3 | 5 | 5 | 1.29 | 1.57 | 2.71 | 4.14 | 5 |
|  | 45 | M | 5 | 1 | 1 | 3 | 5 | 5 | 1 | 1 | 2.43 | 3.57 | 5 |
|  | 48 | M | 5 | 2 | 2 | 3 | 5 | 5 | 2 | 2 | 3.29 | 4.71 | 5 |
|  | 53 | F | 6 | 2 | 2 | 5 | 6 | 6 | 2 | 2 | 5 | 6 | 6 |
|  | 45 | M | 3 | 1 | 1 | 1 | 2 | 3 | 1 | 1 | 1 | 2.29 | 3 |
|  | SUM |  | 123 | 55 | 61 | 87 | 116 | 123 |  |  |  |  |  |
|  | AVERAGE |  | 6.15 | 17.5 | 3.05 | 4.35 | 5.8 | 6.15 | 2.89 | 3.11 | 4.27 | 5.49 | 6.16 |
| Placebo | 49 | M | 6 | 6 | 6 | 6 | 6 | 6 | 6 | 6 | 6 | 6 | 6 |
| Eye | 51 | M | 5 | 4 | 5 | 5 | 5 | 5 | 4.57 | 5 | 5 | 5 | 5 |
| Drops | 50 | M | 5 | 4 | 5 | 5 | 5 | 5 | 4 | 5 | 5 | 5 | 5 |
|  | 54 | F | 8 | 8 | 8 | 8 | 8 | 8 | 7.86 | 8 | 8 | 8 | 8.14 |
|  | 49 | F | 5 | 4 | 5 | 5 | 5 | 5 | 4 | 5 | 5 | 5 | 5 |

TABLE 2-continued

PILOT STUDY - PILOCARPINE 0.5% PLUS BRIMONIDIE 0.2% EYE DROPS
VS. PLACEBO TO REDUCE THE NEED FOR READING GLASSES (X7 DAYS)

| Age | Sex | | | | | | | | | | |
|---|---|---|---|---|---|---|---|---|---|---|---|
| 52 | M | 6 | 6 | 6 | 6 | 6 | 6 | 6 | 6 | 6 | 6 |
| 47 | M | 5 | 5 | 5 | 5 | 5 | 5 | 5 | 5 | 5 | 5 |
| 45 | F | 3 | 3 | 3 | 3 | 3 | 3 | 2.43 | 3 | 3 | 3 |
| 54 | M | 8 | 8 | 8 | 8 | 8 | 8 | 8 | 8 | 8 | 8 |
| 53 | F | 8 | 7 | 8 | 8 | 8 | 8 | 7.29 | 8 | 8 | 8 |
| 49 | F | 6 | 6 | 6 | 6 | 6 | 6 | 5.86 | 6 | 6 | 6 |
| 55 | F | 8 | 8 | 8 | 8 | 8 | 8 | 7.71 | 8 | 8 | 8 |
| 52 | M | 8 | 8 | 8 | 8 | 8 | 8 | 8 | 8 | 8 | 8 |
| 46 | F | 6 | 6 | 6 | 6 | 6 | 6 | 5.29 | 5.86 | 6 | 6 |
| 48 | F | 6 | 6 | 6 | 6 | 6 | 6 | 5.71 | 6 | 6 | 6 |
| 50 | M | 5 | 5 | 5 | 5 | 5 | 5 | 5 | 5 | 5 | 5 |
| 50 | M | 6 | 6 | 6 | 6 | 6 | 6 | 6 | 6 | 6 | 6 |
| 47 | F | 5 | 3 | 5 | 5 | 5 | 5 | 3 | 4.71 | 5 | 5 |
| 54 | M | 10 | 10 | 10 | 10 | 10 | 10 | 10 | 10 | 10 | 10 |
| 45 | F | 3 | 3 | 3 | 3 | 3 | 3 | 2.14 | 3 | 3 | 3 |
| SUM | | 122 | 116 | 122 | 122 | 122 | 122 | | | | |
| AVERAGE | | 6.1 | 5.8 | 6.1 | 6.1 | 6.1 | 6.1 | 5.69 | 6.08 | 6.1 | 6.11 |

The invention claimed is:

1. A method for ameliorating or reducing presbyopia of a patient having an eye, comprising administering to said eye a therapeutically effective amount of an ophthalmic topical preparation comprising a therapeutically effective amount of pilocarpine, or a pharmaceutically acceptable salt thereof, in an amount of 0.25-1.0% and brimonidine, or a pharmaceutically acceptable salt thereof in an amount of 0.05-0.2%.

2. The method of claim 1, wherein pilocarpine is present in an amount of 1% and brimonidine is present in an amount of 0.20%.

3. A method of producing ocular miosis in a subject under normal light conditions which comprises administering to the subject an amount of an ophthalmic preparation comprising a therapeutically effective amount of pilocarpine, or a pharmaceutically acceptable salt thereof, in an amount of 0.25-1.0% and brimonidine, or pharmaceutically acceptable salts thereof, in an amount of 0.05-0.2% effective to produce ocular miosis.

4. A method of ameliorating, reducing or eliminating dimness of vision of a patient having an eye comprising administering to said eye a therapeutically effective amount of an ophthalmic preparation comprising a therapeutically effective amount of pilocarpine, or a pharmaceutically acceptable salt thereof, in an amount of 0. 25-1.0% and brimonidine or a pharmaceutically acceptable salt thereof in an amount of 0.05-0.2%.

5. A method of improving focus and/or correcting refractive errors of a patient having an eye comprising administering to said eye a therapeutically effective amount of an ophthalmic preparation comprising a therapeutically effective amount of pilocarpine, or a pharmaceutically acceptable salt thereof, in an amount of 0. 25-1.0% and brimonidine, or pharmaceutically acceptable salts thereof in an amount of 0.05-0.2%.

6. A method of treating presbyopia in a patient in need of treatment thereof comprising administering an effective amount of an ophthalmic topical preparation comprising a therapeutically effective amount pilocarpine, or a pharmaceutically acceptable salt thereof, in an amount of 0.25-1.0% and brimonidine, or a pharmaceutically acceptable salt thereof in an amount of 0.05-0.2%. to a single eye of a patient thereby leaving the other eye untreated.

* * * * *